United States Patent
Kim et al.

(10) Patent No.: US 10,244,950 B2
(45) Date of Patent: Apr. 2, 2019

(54) BIOLOGICAL INFORMATION DETECTION APPARATUS AND METHOD

(71) Applicant: SAMSUNG ELECTRONICS CO., LTD., Suwon-si (KR)

(72) Inventors: Younho Kim, Hwaseong-si (KR); Jaemin Kang, Seoul (KR); Sangyun Park, Hwaseong-si (KR); Hyoyoung Jeong, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 265 days.

(21) Appl. No.: 14/799,782

(22) Filed: Jul. 15, 2015

(65) Prior Publication Data
US 2016/0015282 A1 Jan. 21, 2016

(30) Foreign Application Priority Data
Jul. 18, 2014 (KR) .......................... 10-2014-0091310

(51) Int. Cl.
| | |
|---|---|
| A61B 5/021 | (2006.01) |
| A61B 5/00 | (2006.01) |
| A61B 5/026 | (2006.01) |
| A61B 5/024 | (2006.01) |
| A61B 5/02 | (2006.01) |

(52) U.S. Cl.
CPC ........ A61B 5/02108 (2013.01); A61B 5/0261 (2013.01); A61B 5/02125 (2013.01); A61B 5/489 (2013.01); A61B 5/6844 (2013.01); A61B 5/7203 (2013.01); A61B 5/7278 (2013.01); A61B 5/02007 (2013.01); A61B 5/02416 (2013.01); A61B 2576/02 (2013.01)

(58) Field of Classification Search
CPC .......................... A61B 5/02108; A61B 5/7203
See application file for complete search history.

(56) References Cited

U.S. PATENT DOCUMENTS

| | | | |
|---|---|---|---|
| 5,255,686 A | 10/1993 | Takeda et al. | |
| 2008/0288036 A1* | 11/2008 | Greenberg | A61N 1/0541 607/115 |
| 2009/0054751 A1* | 2/2009 | Babashan | A61B 5/14552 600/324 |
| 2010/0317945 A1* | 12/2010 | Schraa | A61B 5/1455 600/324 |

(Continued)

FOREIGN PATENT DOCUMENTS

| | | |
|---|---|---|
| JP | 2006102171 A | 4/2006 |
| KR | 101033472 B1 | 5/2011 |

(Continued)

*Primary Examiner* — William J Levicky
(74) *Attorney, Agent, or Firm* — Sughrue Mion, PLLC

(57) ABSTRACT

Provided are biological information detection apparatuses and methods of detecting biological information. The biological information detection apparatus includes a pulse wave measuring unit configured to detect a biological signal of a subject; a height controller configured to adjust a height of the pulse wave measuring unit; and a support member formed on a side of the height controller, wherein the pulse wave measuring unit is further configured to detect the biological signal while the pulse wave measuring unit is spaced apart from a surface skin of the subject by the adjusted height.

7 Claims, 5 Drawing Sheets

(56) References Cited

U.S. PATENT DOCUMENTS

2014/0361147 A1* 12/2014 Fei ................. A61B 5/1455
250/206
2015/0112171 A1* 4/2015 Chang ............... A61B 5/14552
600/323

FOREIGN PATENT DOCUMENTS

KR 101065615 B1 9/2011
KR 101366809 B1 2/2014

* cited by examiner

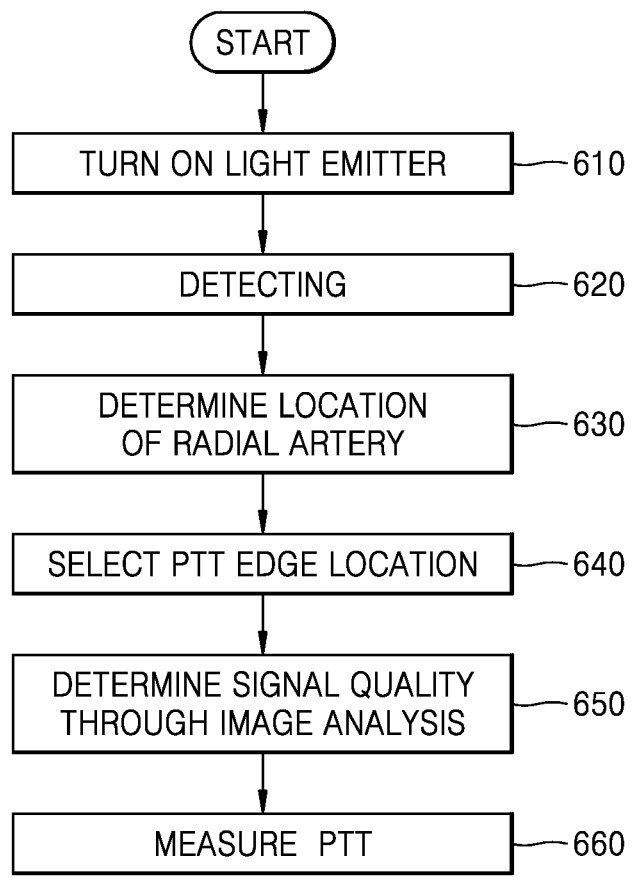

BIOLOGICAL INFORMATION DETECTION APPARATUS AND METHOD

CROSS-REFERENCE TO RELATED APPLICATION

This application claims priority from Korean Patent Application No. 10-2014-0091310, filed on Jul. 18, 2014 in the Korean Intellectual Property Office, the disclosure of which is incorporated herein in its entirety by reference.

BACKGROUND

1. Field

Apparatuses and methods consistent with exemplary embodiments relate to detecting biological information of a subject in a contact or non-contact manner.

2. Description of the Related Art

Various types of apparatuses for detecting biological information of a subject have been developed in line with increased health interests. In particular, as various wearable devices have been widely used, healthcare apparatuses have been developed.

Methods of detecting biological information, such as a pulse wave of a subject, may be largely divided into invasive methods and a non-invasive method. A non-invasive method is widely used because the subject does not experience any pain and a pulse wave can be simply detected.

In order to correctly perform pulse wave analysis (PWA), an optical signal or a pressure signal must be obtained based on information at a certain surface of a subject. Based on this information, biological information of the subject may be obtained and various methods for reducing a measuring error have been used.

SUMMARY

One or more exemplary embodiments provide biological information detection apparatuses that simply detect a pulse wave of a subject.

Further, one or more exemplary embodiments provide methods of detecting biological information of a subject, such as a pulse wave of the subject.

According to an aspect of an exemplary embodiment, there is provided a biological information detection apparatus including: a pulse wave measuring unit configured to detect a biological signal of a subject; a height controller configured to adjust a height of the pulse wave measuring unit; and a support member formed on a side of the height controller, wherein the pulse wave measuring unit is further configured to detect the biological signal while the pulse wave measuring unit is spaced apart from a surface skin of the subject by the adjusted height.

The pulse wave measuring unit may be further configured to detect the biological signal while the support member is in contact with the surface skin of the subject.

The height controller may be further configured to adjust the height of the pulse wave measuring unit to be a zero value, and the pulse wave measuring unit may be further configured to detect the biological signal while the pulse wave measuring unit is in contact with the surface skin of the subject.

The height controller may be further configured to adjust the height of the pulse wave measuring unit to be a non-zero value and the pulse wave measuring unit may be further configured to detect the biological signal when the height controller forms a gap between the pulse wave measuring unit and the surface skin of the subject.

The pulse wave measuring unit may include: a light emitter configured to radiate light onto the subject; and light receivers configured to receive light having the biological signal emitted from the subject.

The light receivers may be respectively formed on two sides of the light emitter.

The light emitter may include a light-emitting diode (LED) or a laser diode, and each of the light receivers may include a photo diode, a photo transistor, or a charge-couple device (CCD).

The support member may be connected to a wearable device, a health-care related device, or a medical device worn by the subject.

The support member may include: a power supply element configured to supply power for operation of the pulse wave measuring unit, and a signal transmission element configured to transmit the biological signal measured by the pulse wave measuring unit to a computing device, wherein the computing device is a data processor or a controller.

The support member may be a rigid PCB (RPCB) or a flexible PCB (FPCB).

According to an aspect of another exemplary embodiment, there is provided a method of detecting biological information including: attaching a biological information detection apparatus to a subject; radiating light onto the subject from the biological information detection apparatus; receiving light reflected from the subject via the biological information detection apparatus; determining a biological information detection location on the subject based on a biological signal detected from the received light; and obtaining biological information based on the biological signal measured at the biological information detection location.

The determining the biological information detection location may include determining a location of a radial artery of the subject and determining at least two locations for simultaneously measuring the biological signals.

The determining the biological information detection location may include determining a location of a radial artery of the subject, and after selecting a first region on the radial artery and a second region separated from the first region and located on the radial artery, simultaneously measuring biological signals at the first and second regions.

The obtaining biological information may include determining a signal quality of the biological signal measured at the biological information detection location, and detecting biological information from the biological signal of which quality has been determined.

The determining the signal quality of the biological signal may include amplifying the biological signal detected from the light receivers or removing noise from the biological signal.

The determining the quality of the biological signal may include repeating the determining the location on the radial artery of the subject when the obtained biological information is determined as not being meaningful.

The biological information may include at least one of an elasticity of a blood vessel, a blood flow velocity, a systolic blood pressure, and a diastolic blood pressure.

According to another aspect of an exemplary embodiment, there is provided a biological information detection apparatus including: an optical signal detector including a light emitter configured to radiate a light onto a skin surface of a subject within a region of an interest (ROI); a first light detector that is disposed at one side end of the light emitter and is configured to detect a light reflected from the ROI; and a second light detector that is disposed at another side end of the light emitter and is configured to detect a light reflected from the ROI; and a height controller that is mounted on the optical signal detector, extended to form a gap between the optical signal detector and the skin surface, and retracted to have the optical signal detector be in contact with the skin surface of the subject.

BRIEF DESCRIPTION OF THE DRAWINGS

The above and/or other aspects will be more apparent and more readily appreciated from the following description of exemplary embodiments, taken in conjunction with the accompanying drawings, in which:

FIG. 6 is a flow chart of a method of detecting biological information by using a biological information detection apparatus according to an exemplary embodiment.

DETAILED DESCRIPTION

Figure 1A:
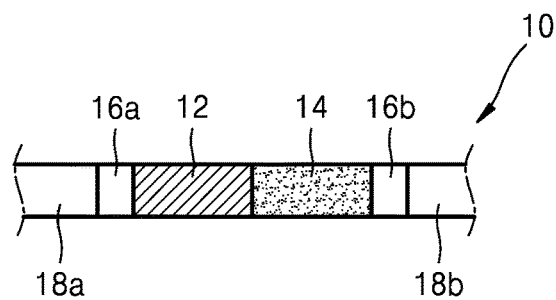
FIGS. 1A, 1B and 1C are views of a biological information detection apparatus according to an exemplary embodiment.

A biological information detection apparatus and a method of manufacturing the biological information detection apparatus according to an exemplary embodiment will now be made in detail to exemplary embodiments, examples of which are illustrated in the accompanying drawings. In the drawings, the widths and thicknesses of layers and regions are exaggerated for clarity. Also, like reference numerals refer to like elements throughout.

Figure 1B:
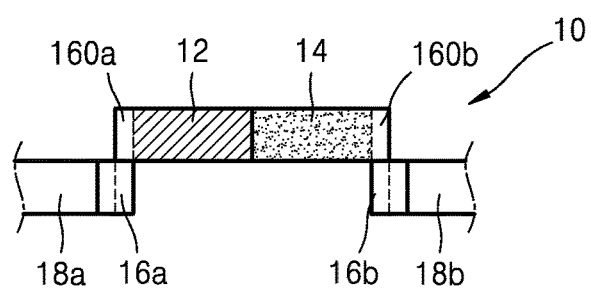
Figure 1C:
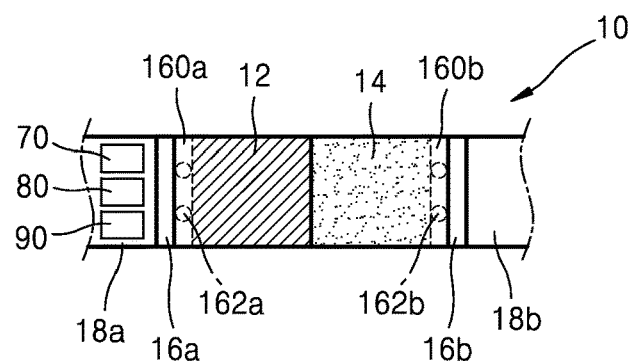

FIGS. 1A, 1B and 1C are views of a biological information detection apparatus 10 according to an exemplary embodiment. FIGS. 1A and 1B are side views of the biological information detection apparatus 10, and FIG. 1C is a plan view of the biological information detection apparatus 10.

Referring to FIG. 1A, the biological information detection apparatus 10 includes pulse wave measuring units 12 and 14, first and second height controllers 16a and 16b formed on at least a side of the pulse wave measuring units 12 and 14, and first and second support members 18a and 18b formed on sides of the first and second height controllers 16a and 16b. The pulse wave measuring units 12 and 14 may be configured to include a light emitter and a light receiver, respectively. The light emitter and the light receiver may be formed to be adjacent to each other. The biological information detection apparatus 10 according to the current embodiment may measure biological information, such as a pulse wave, in contact or non-contact manner with a subject.

Referring to FIGS. 1B and 1C, the pulse wave measuring units 12 and 14 of the biological information detection apparatus 10 may protrude upwards from the first and second height controllers 16a and 16b. The pulse wave measuring units 12 and 14 may include first and second coupling members 160a and 160b that are connected to the first and second height controllers 16a and 16b. The first coupling member 160a may be connected to the first height controller 16a by a first coupling member 162a, and the second coupling member 160b may be connected to the second height controller 16b by a second coupling member 162b. The first and second coupling members 160a and 160b may include screws or coupling pins, but are not limited thereto. According to another exemplary embodiment, each of the first and second coupling members 160a and 160b may include several inner rods inserted inside each other. When the first and second coupling members 160a and 160b extend, each inner rod acts as a guide casting for its upper rod. When the first and second coupling members 160a and 160b are retracted to their shortest length, all the inner rods are accommodated in the first and second coupling members 160a and 160b. Thereby, the first and second coupling members 160a and 160b may be manually extended and retracted. In addition, the first and second coupling members 160a and 160b may be automatically extended and retracted using a motor located at the lower end of the first and second coupling members 160a and 160b.

The biological information detection apparatus 10 of FIGS. 1A, 1B, and 1C may detect biological information, such as a pulse wave while the pulse wave measuring units 12 and 14, the first and second height controllers 16a and 16b, and the first and second support members 18a and 18b are all in contact with a subject. Also, the biological information detection apparatus 10 of FIG. 1B may detect biological information in a state that the first and second height controllers 16a and 16b and the first and second support members 18a and 18b are in contact with the subject and the pulse wave measuring units 12 and 14 are not in contact with the subject.

The first and second support members 18a and 18b may support the pulse wave measuring units 12 and 14, and may be connected to various wearable devices, such as a smart watch or connected to a health care apparatus or medical equipment, or may be included therein. The first and second support members 18a and 18b may be formed of a flexible material, for example, plastic, leather, or fabric to be wearable on a subject. The first and second support members 18a and 18b may support both ends of the pulse wave measuring units 12 and 14, may include a power supply element 70 for supplying power required for operating the pulse wave measuring units 12 and 14, and may include a signal transmission element 80 that transmits a biological signal detected from the pulse wave measuring units 12 and 14 to a computing device 90, such as a data processor or a controller. The first and second support members 18a and 18b may be formed in a structure including a first insulating layer, a conductive layer, and a second insulating layer. The conductive layer may be an electrode structure in which a metal or a conductive material is patterned. The first and second support members 18a and 18b may be formed of a rigid PCB (RPCB) or a flexible PCB (FPCB).

A light emitted diode (LED) or a laser diode may be used as a light source of the light emitter 12 of the pulse wave measuring units 12 and 14. Also, a photo diode, a photo transistor (PTr), or a charge-couple device (CCD) may be used as the light receiver 14 of the pulse wave measuring units 12 and 14. The same descriptions of elements and members will be applied to elements and members of the same names in other drawings.

Figure 2:
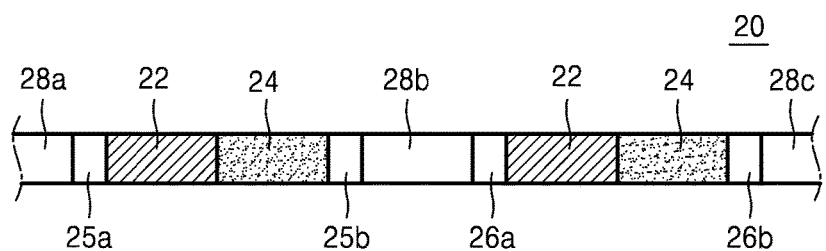
FIG. 2 is a view of a biological information detection apparatus having a plurality of biological information detection units.

FIG. 2 is a view of a biological information detection apparatus 20 having a plurality of biological information detection units.

Referring to FIG. 2, the biological information detection apparatus 20 may include a plurality of pulse wave measuring units 22 and 24. A plurality of support members 28a, 28b, and 28c may be formed on sides of the pulse wave measuring units 22 and 24, and height controllers 25a, 25b, 26a, and 26b may be formed between the pulse wave measuring units 22 and 24 and the support members 28a, 28b, and 28c. The pulse wave measuring units 22 and 24 may be separated from a subject by the height controllers 25a, 25b, 26a, and 26b. In this manner, since the biological information detection apparatus 20 includes a plurality of pulse wave measuring units 22 and 24, biological information, such as a pulse wave may be detected on locations different from each other.

Figure 3A:
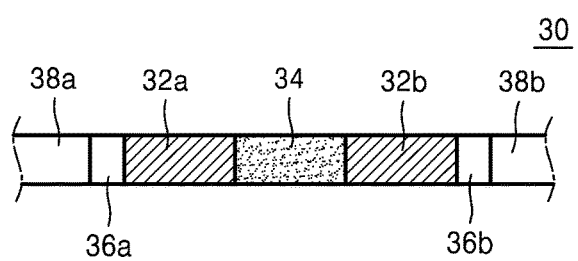
FIGS. 3A and 3B are views of a biological information detection apparatus according to another exemplary embodiment.
Figure 3B:
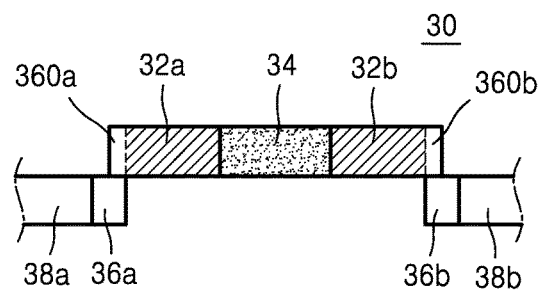

FIGS. 3A and 3B are views of a biological information detection apparatus 30 according to another exemplary embodiment.

Referring to FIG. 3A, the biological information detection apparatus 30 may include pulse wave measuring units 32a, 32b, and 34, first and second height controllers 36a and 36b that are formed on at least a side of the pulse wave measuring units 32a, 32b, and 34, and support members 38a and 38b formed on a side of the height controllers 36a and 36b. In the biological information detection apparatus 30 of FIG. 3A, the pulse wave measuring units 32a, 32b, and 34 include a light emitter 34 and light receivers 32a and 32b formed on two sides of the light emitter 34.

Referring to FIG. 3B, the pulse wave measuring units 32a, 32b, and 34 protrude upwards from the height controllers 36a and 36b. The pulse wave measuring units 32a, 32b, and 34 may include first and second coupling members 360a and 360b that are connected to the height controllers 36a and 36b. The first coupling member 360a may be connected to the first height controller 36a, and the second coupling member 360b may be connected to the second height controller 36b. The first coupling member 360a and the first height controller 36a and the second coupling member 360b and the second height controller 36b respectively may be connected by screws or connection pins.

Figure 4A:
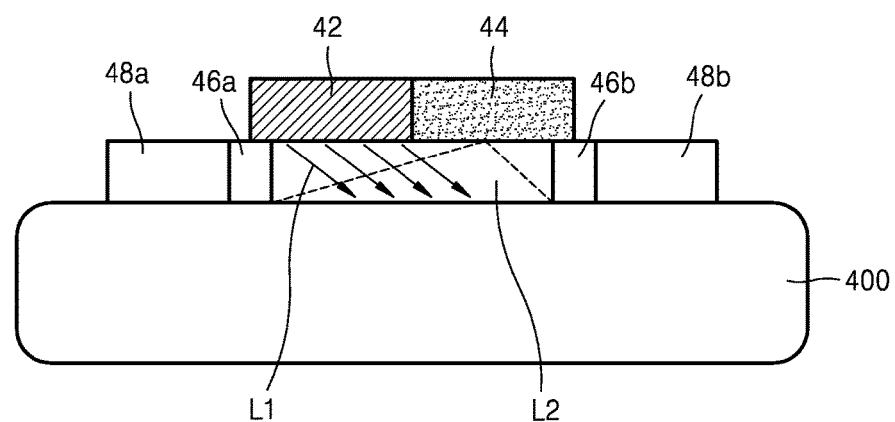
FIGS. 4A and 4B are drawings for illustrating a non-contact type method of detecting biological information by using a biological information detection apparatus according to an exemplary embodiment.
Figure 4B:
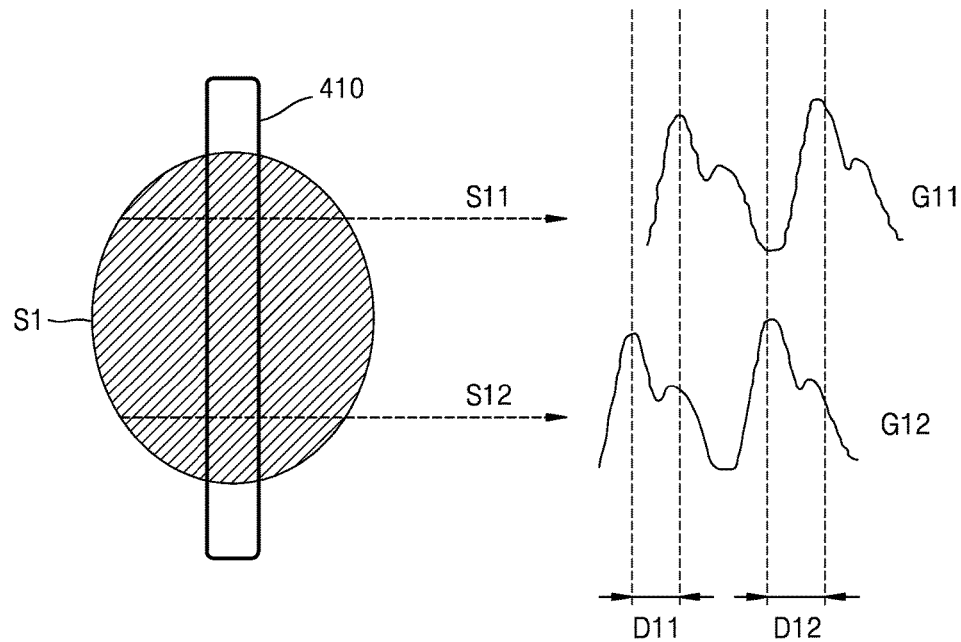

FIGS. 4A and 4B illustrate detecting biological information by a non-contacting method using a biological information detection apparatus according to an exemplary embodiment.

Referring to FIG. 4A, support members 48a and 48b are formed on a subject 400, and pulse wave measuring units 42 and 44 may be located on the height controllers 46a and 46b that are connected to the support members 48a and 48b. The pulse wave measuring units 42 and 44 may be spaced from the subject 400. The light L1 emitted from a light emitter 42 of the pulse wave measuring units 42 and 44 may be radiated onto the subject 400, and light L2 reflected by the subject 400 may be detected at a light receiver 44. A gap between the pulse wave measuring units 42 and 44 and the subject 400 is not specifically limited, for example, the gap may be in a range from about a few mm to about a few cm.

Referring to FIGS. 4A and 4B, the biological information detection apparatus may be attached to a location where biological information of the subject 400 is readily detected, for example, a region adjacent to a radial artery of a wrist. Also, the biological information detection apparatus may be located on a distal end portion of the subject, such as fingers, toes, or earlobes or where density of blood vessel is high or on a carotid artery 410. Hereinafter, a case when the biological information detection apparatus is attached to a radial artery 410 of the subject 400 is described. Light L1, for example, laser light emitted from the light emitter 42 is radiated onto a region where the radial artery 410 of the subject 400 is located. A pulse wave signal is extracted at two locations of a laser speckle range S1 which is a region the laser light L1 emitted from the light emitter 42 is radiated. Here, the speckle range S1 may denote an irregular pattern that is generated by an interference phenomenon at a surface of the subject 400 when the light L1 emitted from the light emitter 42 of the pulse wave measuring units 42 and 44 is radiated onto the subject 400. In the laser speckle range S1, pulse wave signals extracted from a first region S11 and a second region S12 which are regions different from each other may be referred to as G11 and G12. The pulse wave signals G11 and G12 that are extracted from two locations in the laser speckle range S1 of the radial artery 410 of the subject 400 may include biological information, such as elasticity of blood vessel and blood flow velocity of the radial artery 410. Desired information may be obtained by comparing waveforms of the pulse wave signals G11 and G12 at an additional data processor by using the biological information obtained from the light receiver 44 of the pulse wave measuring units 42 and 44 of the biological information detection apparatus. For example, pulse transit time (PTT) information and related time delay (D11 and D12) information may be obtained from the waveforms of the pulse wave signals G11 and G12. Here, the elasticity of blood vessel, blood flow velocity, systolic blood pressure, and diastolic blood pressure of the radial artery 410 may be obtained by using the obtained pulse wave signals G11 and G12 and the PTT.

Figure 5A:
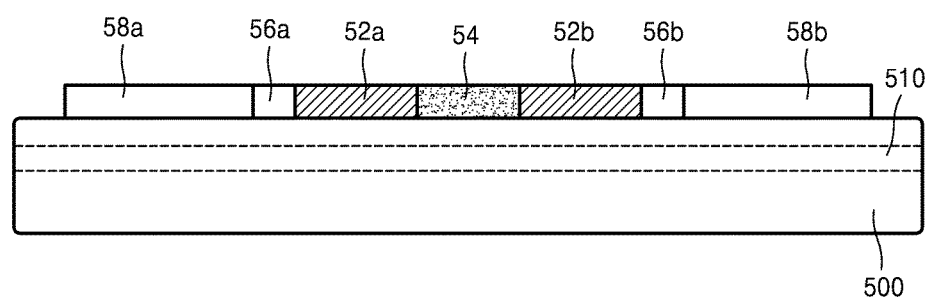
FIGS. 5A and 5B are drawings for illustrating a contact type method of detecting biological information by using a biological information detection apparatus according to an exemplary embodiment.
Figure 5B:
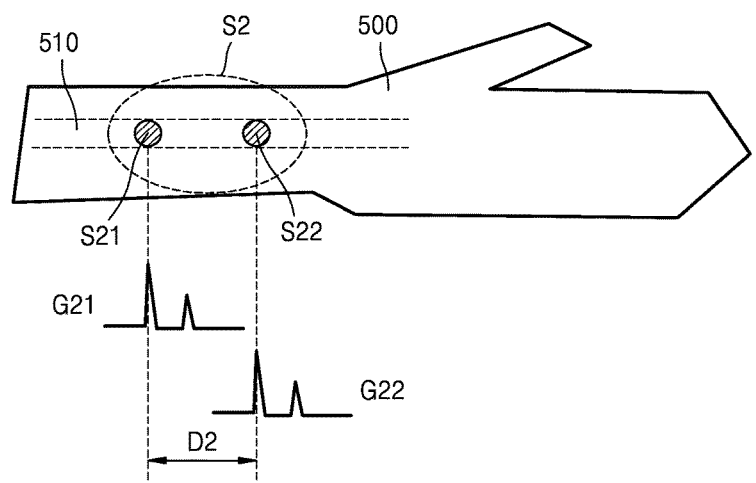

FIGS. 5A and 5B illustrate detecting biological information by a contacting method using a biological information detection apparatus according to an exemplary embodiment.

Referring to FIG. 5A, support members 58a and 58b and pulse wave measuring units 52a, 52b, and 54 that are connected to the support members 58a and 58b through height controllers 56a and 56b may be placed on the body 500 for a medical examination. A light emitter 54 of the pulse wave measuring units 52a, 52b, and 54 may radiate light to a skin surface of the body 500 to exam a vein beneath the skin surface. For example, the pulse wave measuring units 52a, 52b, and 54 are in contact with a body surface of the body 500 under examination so that a light radiated from the pulse wave measuring units 52a, 52b, and 54 may reach a radial artery 510 underneath the body surface. Some of light radiated from the light emitter 54 may be absorbed by the body 500 under examination, and some of the light may be reflected by the body surface or the radial artery 510 of the body 500 under examination. Light reflected by the body 500 under examination may be detected by the light receiver 52a and 52b of the pulse wave measuring units 52a, 52b, and 54.

Referring to FIGS. 5A and 5B, light emitted from the light emitter 54 of the pulse wave measuring units 52a, 52b, and 54 is radiated onto a surface of the subject 500 that includes the radial artery 510. At this point, in an examination region S2 of the body 500 under examination, light reflected at two locations of the radial artery 510 is detected by the light receiver 52a and 52b of the pulse wave measuring units 52a, 52b, and 54. In the examination region S2 of the body 500 under examination, pulse wave signals extracted from a first region S21 and a second region S22 respectively may be referred to as G21 and G22. From the pulse wave signals G21 and G22 extracted from the two locations of the radial artery 510, a time delay D2 may be obtained, and from the time delay D2, a PTT may be obtained. Here, a systolic blood pressure and a diastolic blood pressure may be obtained from the PTT.

As described above, the biological information detection apparatus may optionally detect biological information in a state that pulse wave measuring units contact or non-contact a subject. A method of detecting biological information by using the biological information detection apparatus according to an exemplary embodiment will be described with reference to FIG. 6.

FIG. 6 is a flow chart of a method of detecting biological information by using a biological information detection apparatus according to an exemplary embodiment.

Referring to FIGS. 4A, 4B, and 6, the biological information detection apparatus according to an exemplary embodiment is attached to the body 400 under examination. The support members 48a and 48b of the biological information detection apparatus may be attached to a surface of the body 400 under examination, and thus, the biological information detection apparatus is fixed while the biological information is detected. After the biological information detection apparatus is fixed on the surface of the subject, a biological information detecting operation begins.

First, the light emitter 42 is turned on by driving a laser or a light-emitting diode of the light emitter 42 by supplying power to the light emitter 42 of the pulse wave measuring units 42 and 44 (operation 610). Next, a laser light L1 emitted from the light emitter 42 is radiated onto an irradiation region on a surface of the body 400 under examination, and light L2 reflected or scattered from the body 400 under examination is detected by the light receiver 44 of the pulse wave measuring units 42 and 44 (operation 620).

Next, a biological information detection location is determined by a computing device, such as a data processor or a controller, by using the signal detected by the light receiver 44 of the pulse wave measuring units 42 and 44. For example, after determining a location of the radial artery 410 (operation 630), and a PTT edge location may be selected (operation 640). Generally, the location of the radial artery 410 of the body 400 under examination may be empirically predicted in advance. However, a further precise location may be controlled from a biological signal detected by the light receiver 44. After the location of the radial artery 410 is determined, at least two locations from which a biological signal can be simultaneously detected are selected from the radial artery 410. This is referred to as an operation of selecting a PTT edge location (operation 640). In order to obtain information, such as a pulse wave or a PTT by using biological signals obtained from two locations of the radial artery 410, it is advantageous to obtain biological information of regions that are separated from each other as far as possible in the examination region S1. Accordingly, in order to obtain PTT information, two locations that are separated from each other as far as possible may be selected in the examination region S1, and this is referred to as an operation of selecting a PTT edge location. For example, in order to obtain PTT information, the first region S11 and the second region S12 of the radial artery 410 may be selected by a PTT edge location selection process. After selecting the first region S11 and the second region S12 of the radial artery 410 in the examination region S1, a pulse wave signal may be simultaneously detected from the first region S11 and the second region S12.

After determining the biological information detection location, biological information may be obtained by measuring the biological signal. The pulse wave signals measured according to time in the first region S11 and the second region S12 of the radial artery 410 respectively may be referred to as G11 and G12, and signal quality may be determined through analyzing images of the pulse wave signals G11 and G12 (operation 650). In order to have the above analysis, an operation of amplifying the biological signal detected by the light receiver 44 of the pulse wave measuring units 42 and 44 or removing noise from the biological signal may be performed at the same time. In the signal quality determining process, when the biological signal obtained is determined as not meaningful, the analyzing process may be restarted from the operation of determining of location on the radial artery 410 (operation 630) or the operation of determining a PTT edge location (operation 640). Next, an operation of measuring PTT may be performed by using the biological signals that are simultaneously measured at the two locations of the radial artery 410 of the body 400 under examination, and afterwards, biological information detection may be obtained from the measured PTT. That is, biological information, such as elasticity of blood vessel, blood flow velocity, systolic blood pressure, and diastolic blood pressure of the radial artery 410 of the body 400 under examination may be obtained by using the pulse wave and PTT information. For example, a systolic blood pressure and a diastolic blood pressure of a blood vessel may be measured by using an already known PTT base blood pressure prediction algorithm.

Here, in order to explain the method of detecting biological information as shown in FIG. 6, as depicted in FIGS. 4A and 4B, the pulse wave measuring units 42 and 44 are separated from a surface of the body 400 under examination. However, the current embodiment is not limited thereto. That is, as depicted in FIGS. 5A and 5B, the method described in FIG. 6 may also be applied to a case when the pulse wave measuring units 52a, 52b, and 54 are in contact with the body 500 under examination to detect biological information.

As described above, according to the exemplary embodiments, biological signals may be readily measured at least two locations of a subject by using contact and non-contact methods. Thus, correct biological information values may be detected by using the measured biological signals.

According to an exemplary embodiment, a biological information detection apparatus and method are provided. According to the biological information detection apparatus and method, biological signals may be readily measured at least two locations of a subject in contact and non-contact type manners. Thus, a correct biological information value may be detected by using the measured biological signals.

The foregoing exemplary embodiments are merely exemplary and are not to be construed as limiting. The present disclosure can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A biological information detection apparatus comprising:
   a light emitter configured to emit a light onto a subject;
   a light receiver configured to detect a biological signal from the light that returns from the subject after being emitted onto the subject;
   a height controller coupled with a pair of the light emitter and the light receiver that is connected to the light emitter side-by-side; and a support member disposed on a side of the height controller and configured to be in contact with a surface skin of the subject;

wherein the height controller is configured to lift up and down the pair of the light emitter and the light receiver together to adjust a height of the light emitter from support member and a height of the light receiver from the support member to be a same height from the support member, and wherein, when the height controller lifts up the pair of the light emitter and the light receiver, the pair of the light emitter and the light receiver are disposed at a level different from the support member.

2. The biological information detection apparatus of claim 1, wherein the light receiver is further configured to detect the biological signal while the support member is in contact with the surface skin of the subject and the light emitter and the light receiver are spaced apart from the surface skin of the subject.

3. The biological information detection apparatus of claim 1, wherein the light emitter comprises a light-emitting diode or a laser diode, and the light receiver comprises a photo diode, a photo transistor, or a charge-couple device.

4. The biological information detection apparatus of claim 1, wherein the support member is configured to be connected to a wearable device, a health-care related device, or a medical device worn by the subject.

5. The biological information detection apparatus of claim 1, wherein the biological information detection apparatus further comprises a computing device, and wherein the support member comprises:

a power supply element configured to supply power for operation of the light emitter and the light receiver, and a signal transmission element configured to transmit the biological signal detected by the light receiver to the computing device.

6. The biological information detection apparatus of claim 1, wherein the support member is a rigid printed circuit board or a flexible printed circuit board.

7. A biological information detection apparatus comprising, a light emitter configured to emit a light onto a subject;

a first light receiver configured to receive the light that returns from the subject after being emitted onto the subject; and a second light receiver configured to receive the light that returns from the subject after being emitted onto the subject;

wherein the light emitter is disposed between the first light receiver and the second light receiver, and is in contact with the first light receiver and the second light receiver, and wherein the biological information detection apparatus further comprises:

a first height controller connected to the first light receiver;

a second height controller connected to the second light receiver;

wherein the first height controller and the second height controller are configured to lift up and down the light emitter and the first and second light receivers together so that the light emitter, the first light receiver, and the second light receiver have a same height.

* * * * *